United States Patent
Kirchhuebel et al.

(10) Patent No.: US 6,788,455 B2
(45) Date of Patent: Sep. 7, 2004

(54) MICROSCOPE FOR THE WIDE-ANGLE VIEWING, IN PARTICULAR FOR EYE SURGERIES

(75) Inventors: Rainer Kirchhuebel, Asslar (DE); Josef Reiner, Cologne (DE)

(73) Assignee: Oculus Optikgeraete GmbH, Wetzlar-Dutenhofen (DE)

(*) Notice: Subject to any disclaimer, the term of this patent is extended or adjusted under 35 U.S.C. 154(b) by 41 days.

(21) Appl. No.: 10/023,783

(22) Filed: Dec. 17, 2001

(65) Prior Publication Data
US 2002/0118448 A1 Aug. 29, 2002

(30) Foreign Application Priority Data
Dec. 23, 2000 (DE) ................................. 200 21 955 U (51) Int. Cl.$^7$ .......................... G02B 21/00; A61B 3/00
(52) U.S. Cl. ................. 359/381; 359/368; 351/219
(58) Field of Search ............... 359/368–390; 351/295, 219

(56) References Cited

U.S. PATENT DOCUMENTS

| | | | | |
|---|---|---|---|---|
| 4,015,898 A | * | 4/1977 | Schirmer | 351/221 |
| 4,518,231 A | * | 5/1985 | Muchel et al. | 359/377 |
| 5,009,487 A | | 4/1991 | Reiner | 359/431 |
| 5,200,773 A | * | 4/1993 | Volk | 351/219 |
| 5,282,085 A | | 1/1994 | Volkert et al. | 359/322 |
| 5,321,447 A | | 6/1994 | Sander et al. | 351/216 |
| 5,438,456 A | * | 8/1995 | Grinblat | 359/835 |
| 5,526,074 A | * | 6/1996 | Volk | 351/219 |
| 5,699,193 A | * | 12/1997 | Monno et al. | 359/630 |
| 5,793,524 A | * | 8/1998 | Luloh | 359/381 |
| 6,212,006 B1 | * | 4/2001 | Reiner | 359/388 |

FOREIGN PATENT DOCUMENTS

| | | | | |
|---|---|---|---|---|
| DE | 35 39 009 | * | 5/1987 | 359/368 |
| DE | 89 02 035.9 | | 5/1989 | |
| DE | 94 15 219.5 | | 1/1995 | |
| EP | 1 191 381 | | 3/2002 | |
| WO | WO 91/15150 | | 10/1991 | |

* cited by examiner

*Primary Examiner*—Thong Q Nguyen
(74) *Attorney, Agent, or Firm*—Flynn, Thiel, Boutell & Tanis, P.C.

(57) ABSTRACT

Provisions must be made in surgery microscopes for eye surgeries through the selective adding of optics so that a non-reversed and erect-standing image can be produced including that of the fundus of the eye. A device for the image reversion is fastened on the microscope so that it can be moved into the beam path and is then provided between the lens and the eye so that the overall height of the microscope is not influenced. This inventive arrangement can be utilized very universally on very differently designed microscopes and can be operated with prism systems of varying designs.

17 Claims, 15 Drawing Sheets

MICROSCOPE FOR THE WIDE-ANGLE VIEWING, IN PARTICULAR FOR EYE SURGERIES

FIELD OF THE INVENTION

The invention relates to a microscope for the wide-angle viewing of an eye with an optical device provided between the lens and the eye to be treated, and which creates a reversed image for viewing the fundus of the eye, in particular for eye surgeries and, more particularly with an optical device for image reversion and image erection, which device lies in, or preferably can be moved or swung into, the beam or viewing path of the microscope.

BACKGROUND OF THE INVENTION

A wide-angle viewing of the eye can take place in a simple manner through the use of a contact lens placed directly onto the eye. However, it is also possible to mount a separate optical device, which is spaced from the eye, on the microscope. If aspheric lenses are used for this purpose, which lenses guarantee alone a sufficient wide-angle viewing, then a side-reversed, upside-down image is created in the microscope just as this is the case with the contact lens, which image is acceptable for diagnostic purposes; however, during eye surgeries, which must be carried out advantageously at least at times also with a wide-angle viewing under stereo observation, a reversed stereopsis is created so that even experienced surgeons cannot be expected to handle such a control technique.

It is also already known to provide in such a microscope a device for the image reversion and image erection, as this is shown in the DE Patent No. 38 26 069 C2 (corresponding to U.S. Pat. No. 5 009 487). It is thereby particularly important that the additional structural parts do not significantly increase the height of the microscope because the surgeon must carry out the surgery and must look through the microscope at the same time, and the distance between the eyepiece of the microscope and the eye of the patient can therefore not be increased at random. Furthermore, the optical device for image reversion and image erection is, however, also supposed to be moved is quickly as possible into and out of the beam path of the microscope so that work can be done both in the front section of the eye and also in the fundus of the eye without having to change the microscope.

SUMMARY OF THE INVENTION

The purpose of the invention is therefore to design a microscope of the type identified in greater detail above so that its height does not significantly increase not even when it can be operated selectively with an optical device for image reversion and image erection.

The purpose is attained according to the invention in such a manner that the optical device for image reversion and image erection consists of a reflecting system with a low height in particular a prism system which is carried by a bolder fastened on the microscope, and can thus be moved or swung into the beam path of the microscope between the lens and the eye to be treated, that the prism system is provided directly in front of the lens at a distance from the eye. The arrangement of the invention utilizes the space existing between the lens and the eye to be treated so that the total overall height of the microscope is maintained even when a non-reversed and upright image is created in the eyepiece. It is thereby of no importance in which manner the wide-angle viewing is produced: the optical device for viewing the fundus of the eye can both be mounted on the holder for the prism system and can also be designed to be placed directly onto the eye. A non-reversed and upright image is in this manner created immediately after the swinging in or moving in of the optical device, which image must not be created only after a further operation. In other words, manual or foot operation otherwise needed for this is eliminated, which is of a great advantage especially during eye surgery.

The optical device for the image reversion and image erection can be inserted into the area between the lens and the eye. However, it is significantly easier when the holder is rotatable about a swivel axis arranged on the underside of the microscope so that only a few parts are needed in order to swing the optical device from a position ready to operate into the beam path of the microscope. The prism system is thereby preferably arranged in a closed housing which has openings therethrough for the beam path. In addition, a projection lens for adjusting the beam path can be provided between the prism system and the lens, preferably in the opening of the housing adjacent to the lens, which projection lens is directly adjacent to the lens after the holder for the prism system has been moved or swung into the beam path of the microscope. Moreover it is advantageous when the swivel axle for the holder is provided approximately horizontally on the microscope. In other embodiments the swivel axle can be oriented vertically.

The optical device for the (wide-angle) viewing of the fundus of the eye can consist of a lens system movably arranged along the beam path. The distance of this lens system from the eye can be left unchanged by the surgeon during his work when for focusing a movable optical device is provided in the beam path between the optical device for viewing the fundus of the eye and the prism system, which optical device is movable along the beam path and relative to the prism system; one single optical lens, which itself can be focused, is already sufficient for this purpose.

It is advantageous when for focusing both optical devices can be operated for wide-angle viewing and/or for adjusting the intermediate image by means of manually or electromotively driven spindle drives. Thus it is, for example, possible to move the optical device for viewing the fundus of the eye by means of a first spindle drive fastened on the holder along the beam path, best in such a manner that the optical device is held on a carriage which is guided longitudinally movably on a guide pin mounted on the holder and extending parallel to the first spindle drive, whereby a first control knob for the first spindle drive is supported on the guide pin. The entire adjustment mechanism for the optical device is in this manner connected to the holder and thus also to the prism system, and is at all times exactly adjusted.

The optical device for adjusting the intermediate image can be handled in a similar manner when same can be moved along the beam path by means of a second spindle drive fastened on the guide pin, whereby a second control knob is used for this purpose.

The prism system can be designed, for example, as a reflection prism according to Uppendahl or Schmidtpechan.

The control knobs for the spindle drives can be manually operated; however, they can be operated in an advantageous manner by means of an electric drive, whereby such a drive has, for example, an electric motor preferably provided on the holder, the output of which electric motor can be rotationally coupled to the control knob through a flexible shaft so that the switching on and off can be done, if desired, with a foot-operated switch so that the surgeon will be able to keep his hands free when refocusing must take place.

BRIEF DESCRIPTION OF THE DRAWINGS

The invention will be further discussed hereinafter by reference to one exemplary embodiment illustrated in the accompanying drawings, in which.

DETAILED DESCRIPTION

An eyepiece 1 according to FIGS. 1–10 is first of all provided on a microscope according to the invention, which eyepiece is pivotal about an axle 2 so that, for example during eye surgery, the surgeon can adjust at an optimum the eyepiece 1 to his posture during surgery. Furthermore, an adjustment knob 3 is provided on the microscope to facilitate a change in the enlargement factor. A lens 4 enables first of all the viewing of the front section 5 of an eye 6.

An optical device 8 for viewing the fundus of the eye 9 is mounted on an attachment 7 of the microscope in the vicinity of the lens 4, which optical device 8 can be swung into the beam path 10 of the microscope and can be moved in direction of the beam path 10 by means of a (first) spindle drive 11, This optical device 8, here a simple observation lens, is mounted on a holder 12 which is pivotal about a swivel axle 13 which is stationary on the attachment 7. The optical device 8 is fastened to a (first) carriage 14 which is movably guided on a guide pin 15 that extends parallel to the beam path 10 below the lens 4. The carriage 14 is moved by a not illustrated traveling nut in a segment 16 of the carriage 14 which engages the threaded spindle 17. The guide pin 15 and the threaded spindle 17 are hastened at one end in a common bearing piece 18 affixed to the holder 12 and at the other end in a (first) connecting plate 19. The threaded spindle 17 is rotatably supported for movement about its axis. A (first) control knob 20 is provided in connection with the threaded spindle 17, with the help of which control knob the spindle drive 11 can be initiated so that the optical device e will be moved along the beam path 10. The optical device 8 is fastened to a holding bolt 22 which is held resiliently in a guideway 21. The entire spindle drive can be separated from the holder 12 at the bearing piece 18 so that same can be sterilized.

Figure 1:
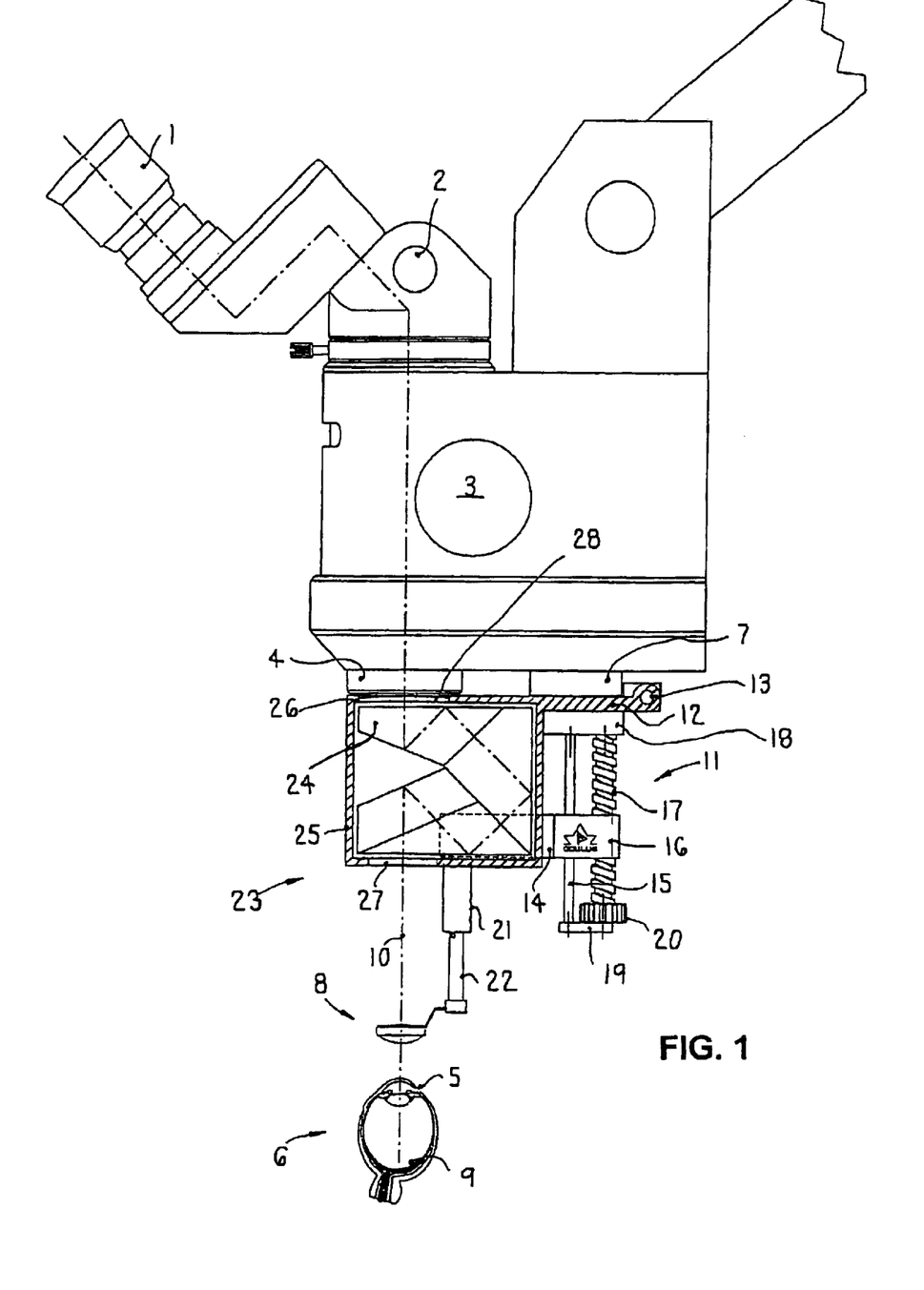
FIG. 1 is a side view of an inventive microscope provided with a prism system and an optical device for wide-angle viewing according to Uppendahl.

A device 23 for the image reversion and image erection, which device is connected to the optical device 8 through a common holder 12, consists of a Uppendahl prism system 24 in FIG. 1 and a housing 25 housing the prism system 24. The housing 25 can be designed in one piece with the holder 12 and the bearing piece 18. The bearing piece 18 is advantageously designed to be removable from the holder 12.

Each opening 26, 27 in the housing 25 permits the passage of the beam path 10 through the prism system 24. A projection lens 28 in the opening 26 adjacent to the lens 4 for adjusting the beam path 10, which is significantly extended because of the prism system 24, is connected in front of the entry of the beam path 10 into the prism system 24.

Figure 2:
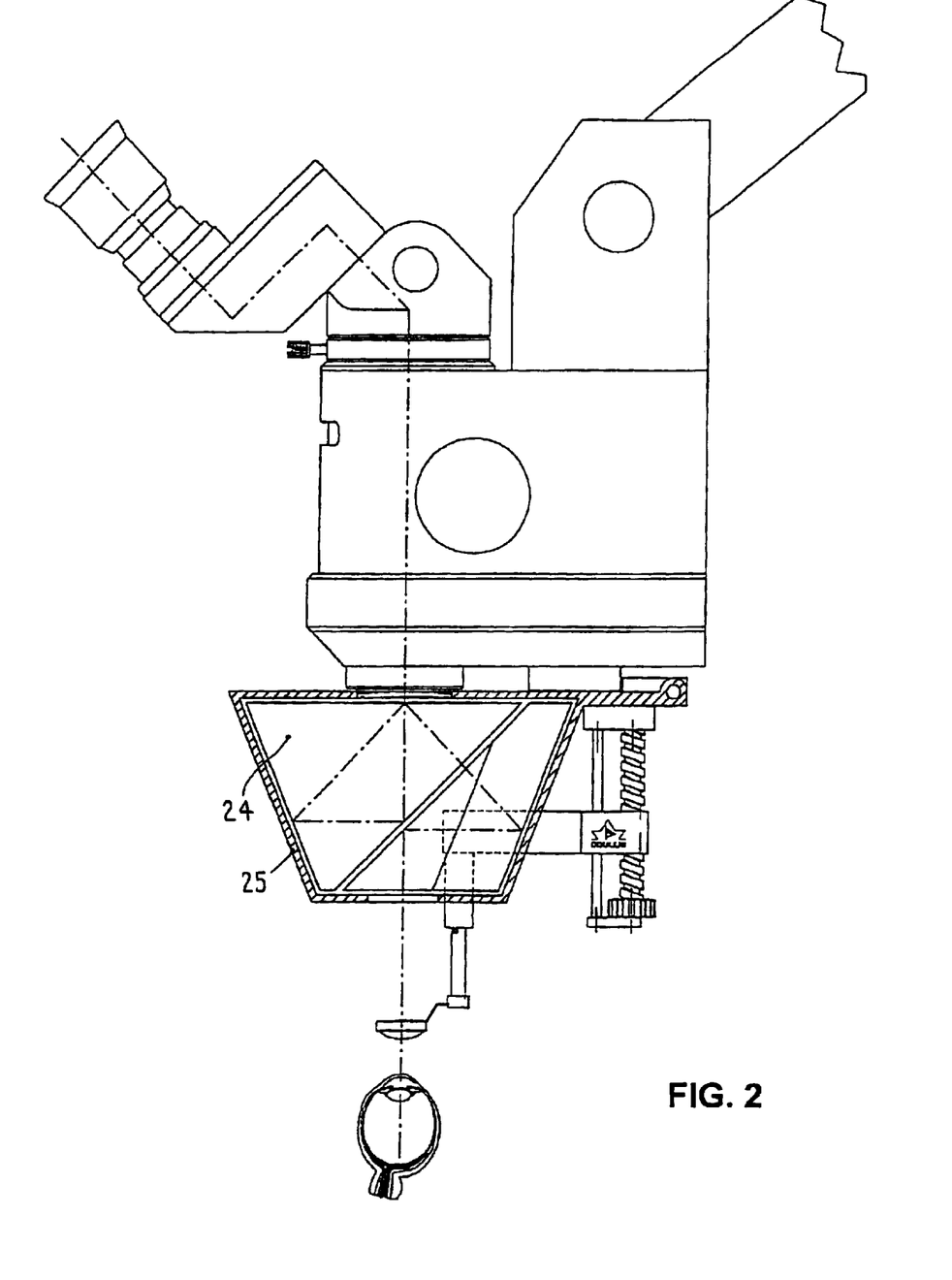
FIG. 2 illustrates a microscope according to FIG. 1, however, with a prism system according to Schmidtpechan.

Corresponding with the prism system 24 according to Schmidtpechan utilized in FIG. 2, the housing 25 is there formed or shaped slightly differently, however, the arrangement otherwise does not differ from the arrangement of FIG. 1.

Figure 3:
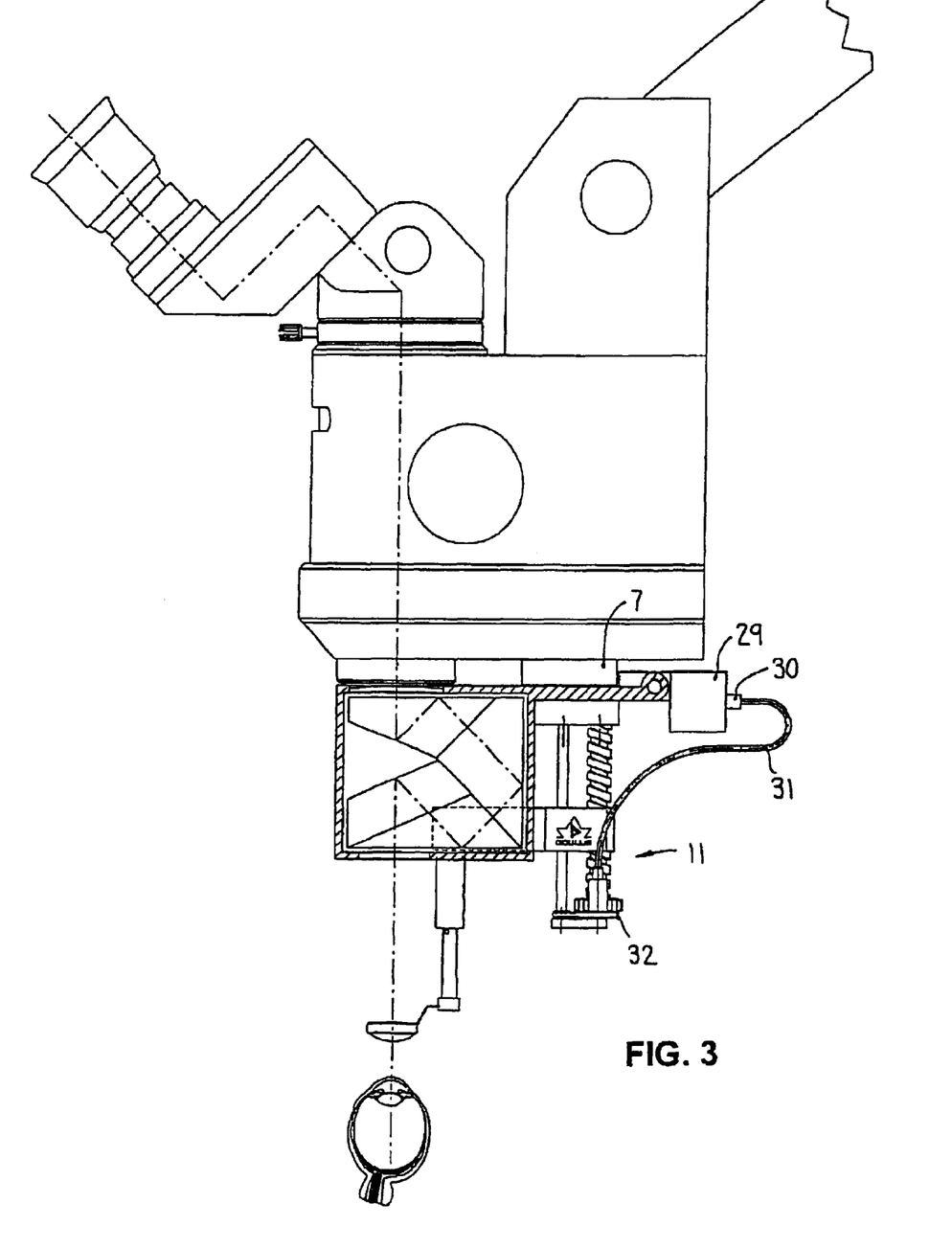
FIG. 3 illustrates a microscope according to FIG. 1 including an electric drive for the optical device for wide-angle viewing.
Figure 4:
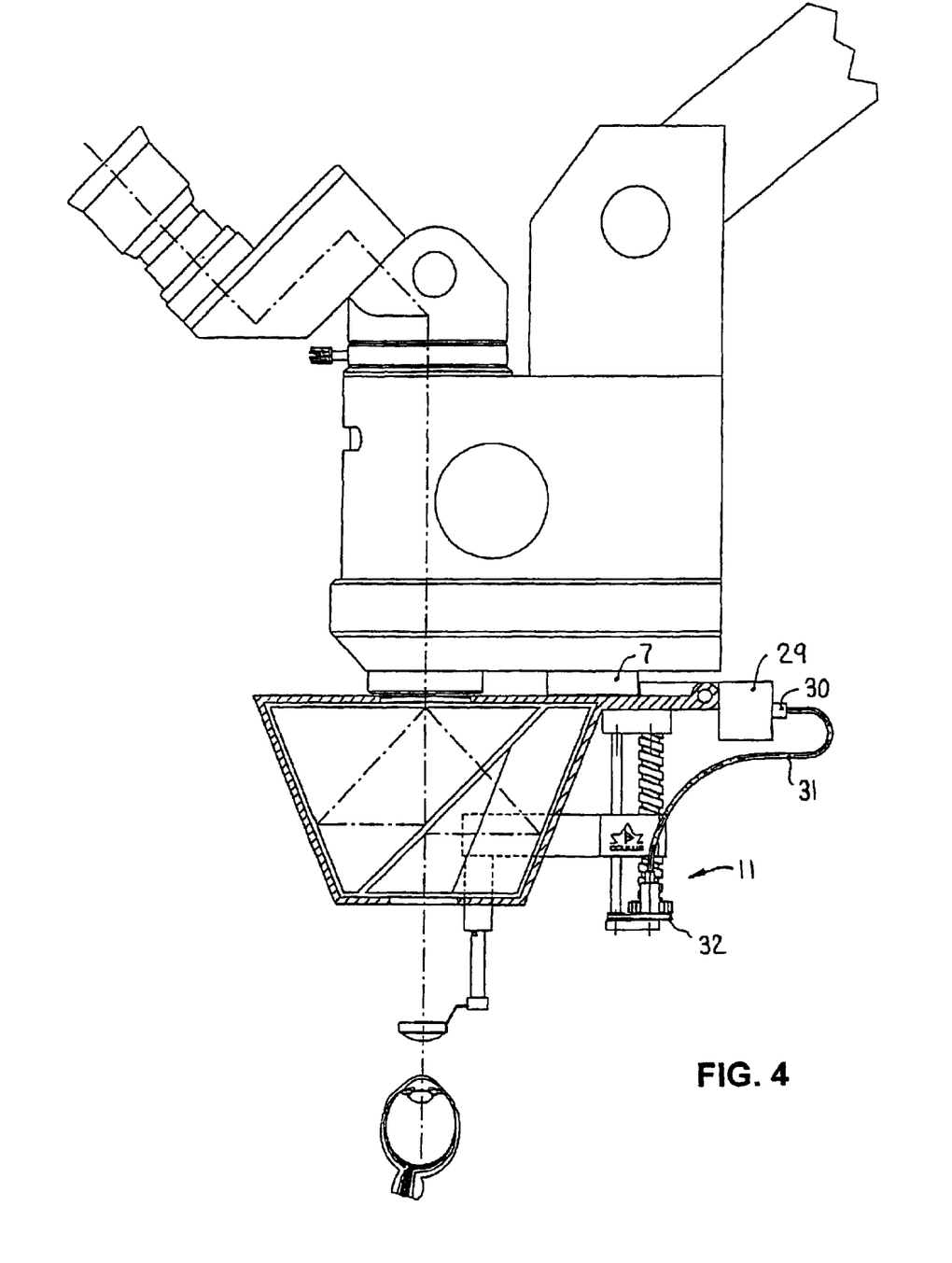
FIG. 4 illustrates a microscope according to FIG. 2 including an electric drive for the optical device.

The spindle drive 11 in FIGS. 3, 4 is equipped with an electromotive drive. An electric motor 29 is for this purpose provided on the attachment 7, from the output of which motor the threaded spindle 17 can be rotated through a flexible shaft 31 connectable by means of a suitable coupling 30 and a belt drive 32. The electric motor can also be mounted at a different area of the system. Thus, it is sufficient to switch the electric motor 29 using a foot switch in order to move the optical device 8 along the beam path 10; for example, a surgeon can focus accordingly without having to put down his surgical tools and thus having to interrupt the ongoing surgery.

Figure 5:
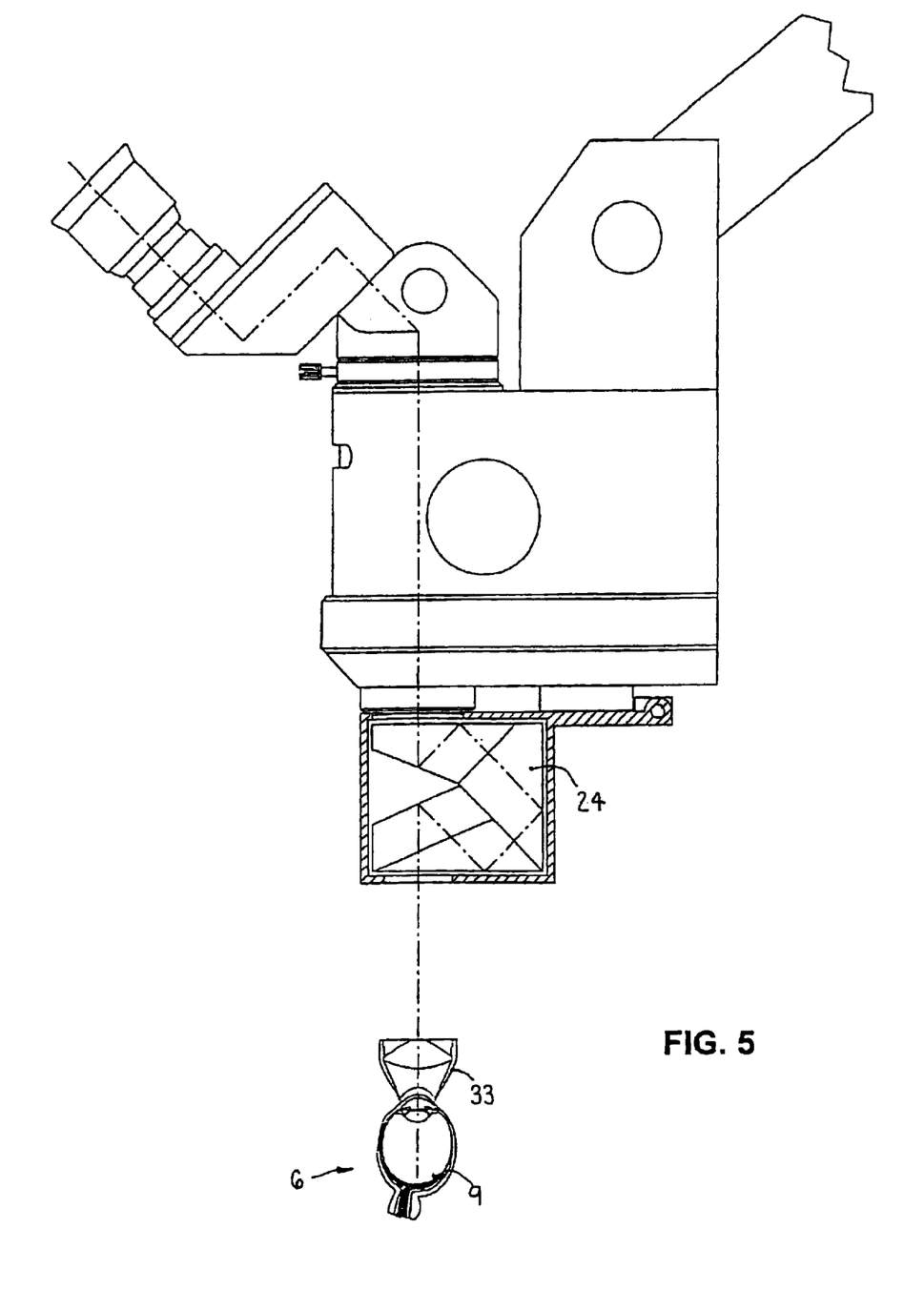
FIG. 5 illustrates a microscope according to FIG. 1 with an optical device for wide-angle viewing, which optical device has been changed compared to FIG. 3.
Figure 6:
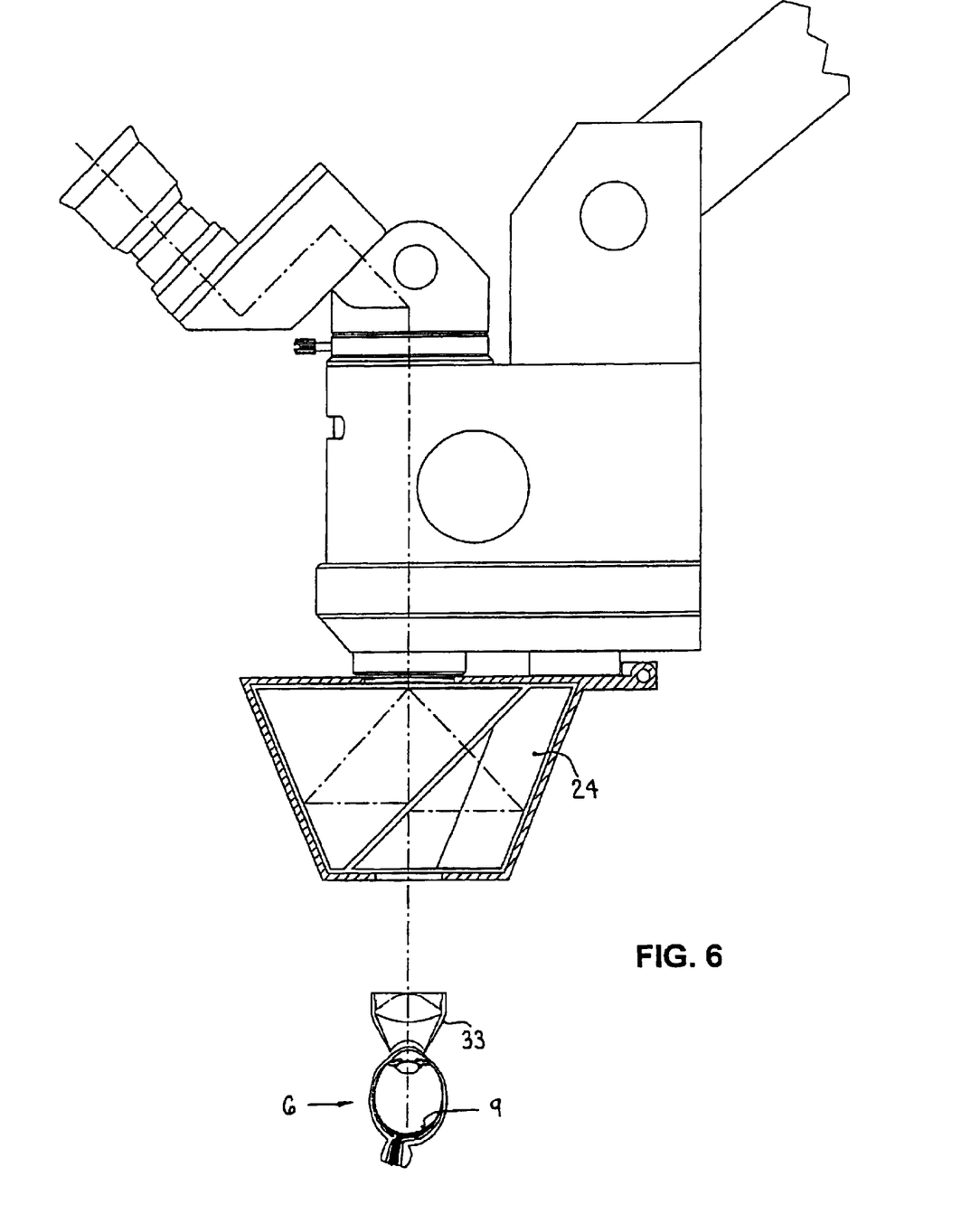
FIG. 6 illustrates a microscope according to FIG. 2 with an optical device for wide-angle viewing, which optical device has been changed compared to FIG. 4.

The invention can also be utilized when, instead of a non-contact viewing as this is the case in the arrangements of FIGS. 1–4 by means of the optical device 8, according to FIGS. 5, 6, an aspheric optical device 33 is placed directly onto the eye 6, which in a similar manner as the optical device 8 delivers initially a reversed and upside-down image of the fundus of the eye 9, which in turn is utilized by the prism system 24.

Figure 7:
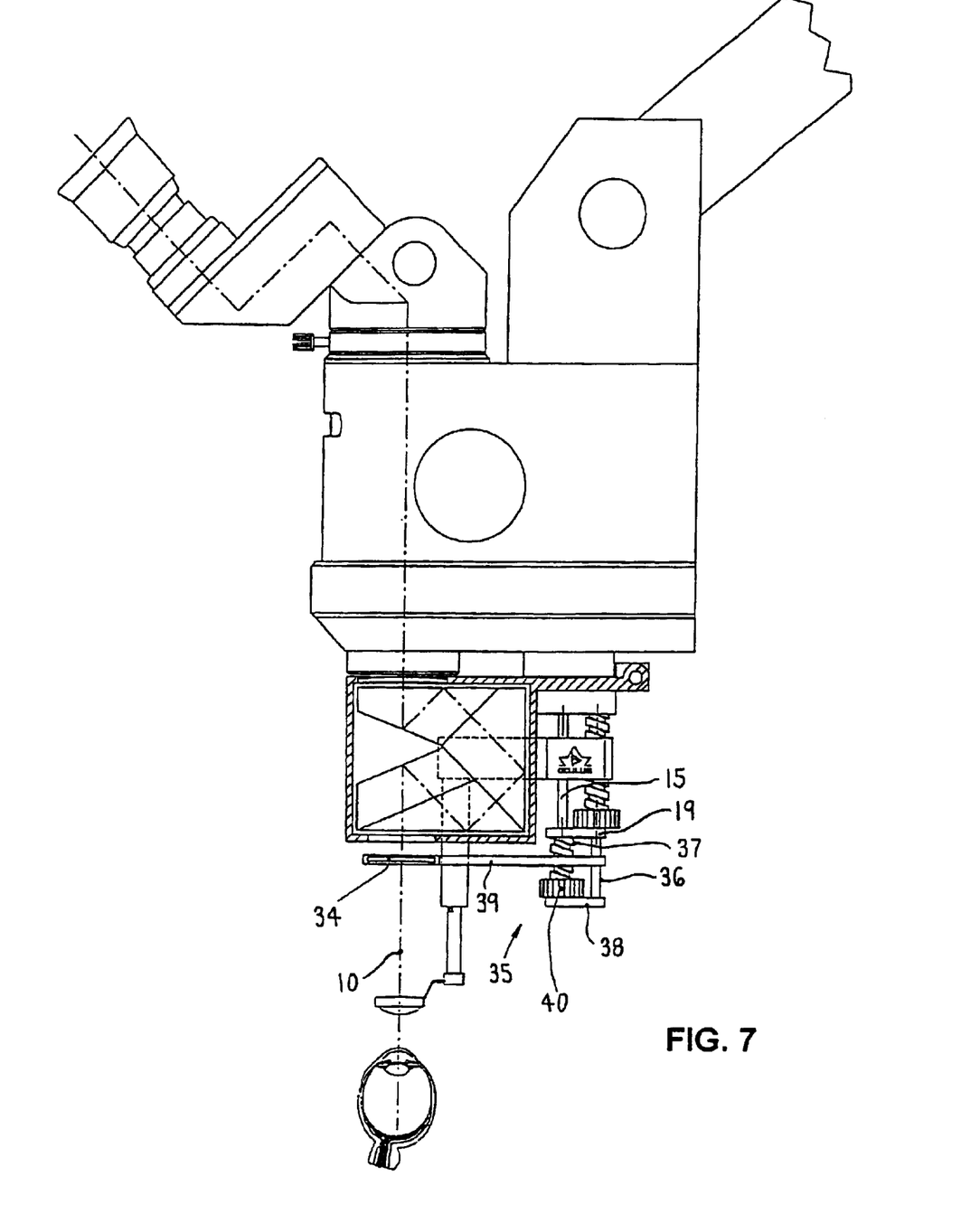
FIG. 7 illustrates a microscope according to FIG. 1 with a manually drivable optical device to adjust the intermediate image.
Figure 8:
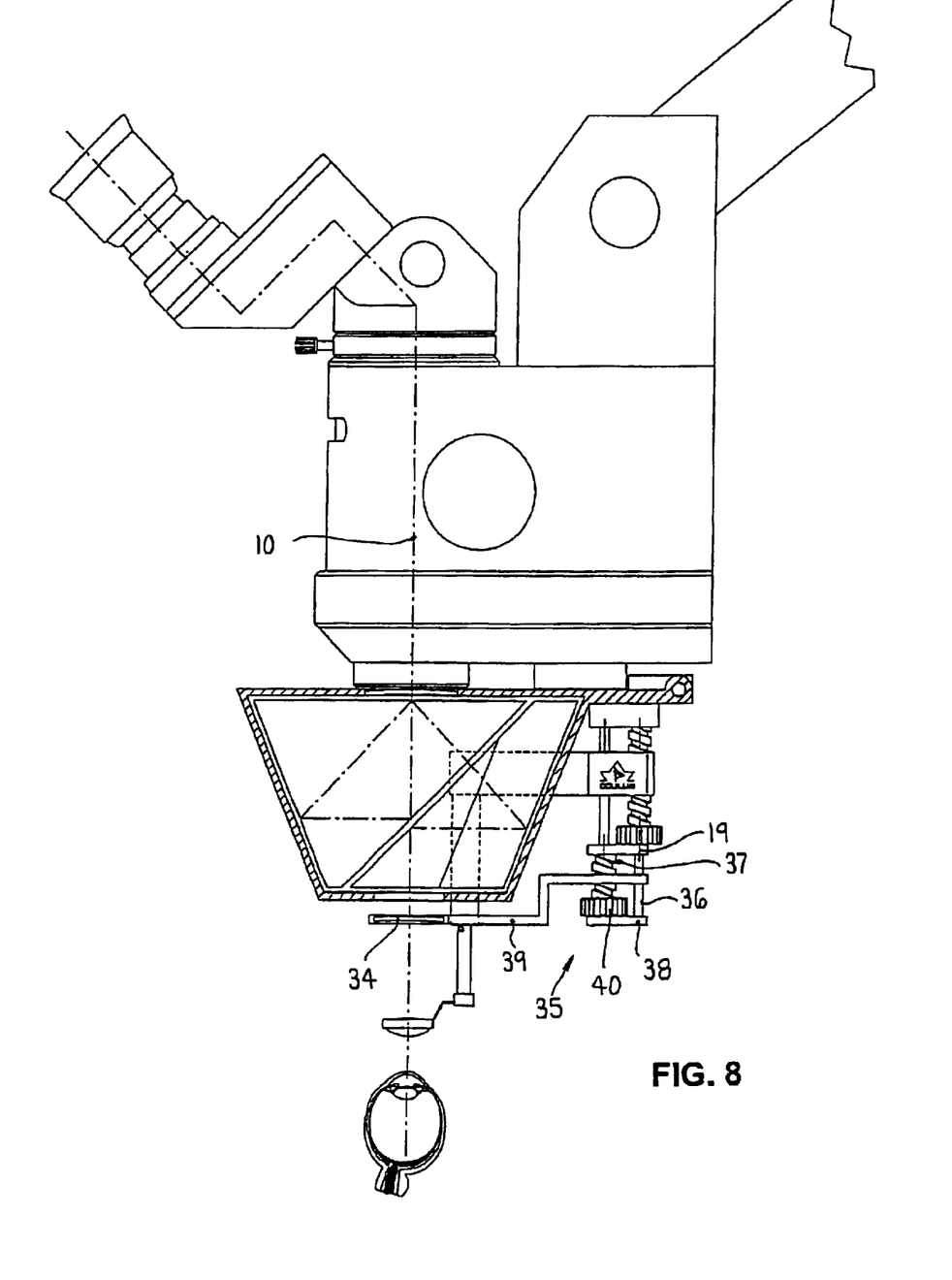
FIG. 8 illustrates a microscope according to FIG. 2 with a manually drivable optical device to adjust the intermediate image.
Figure 9:
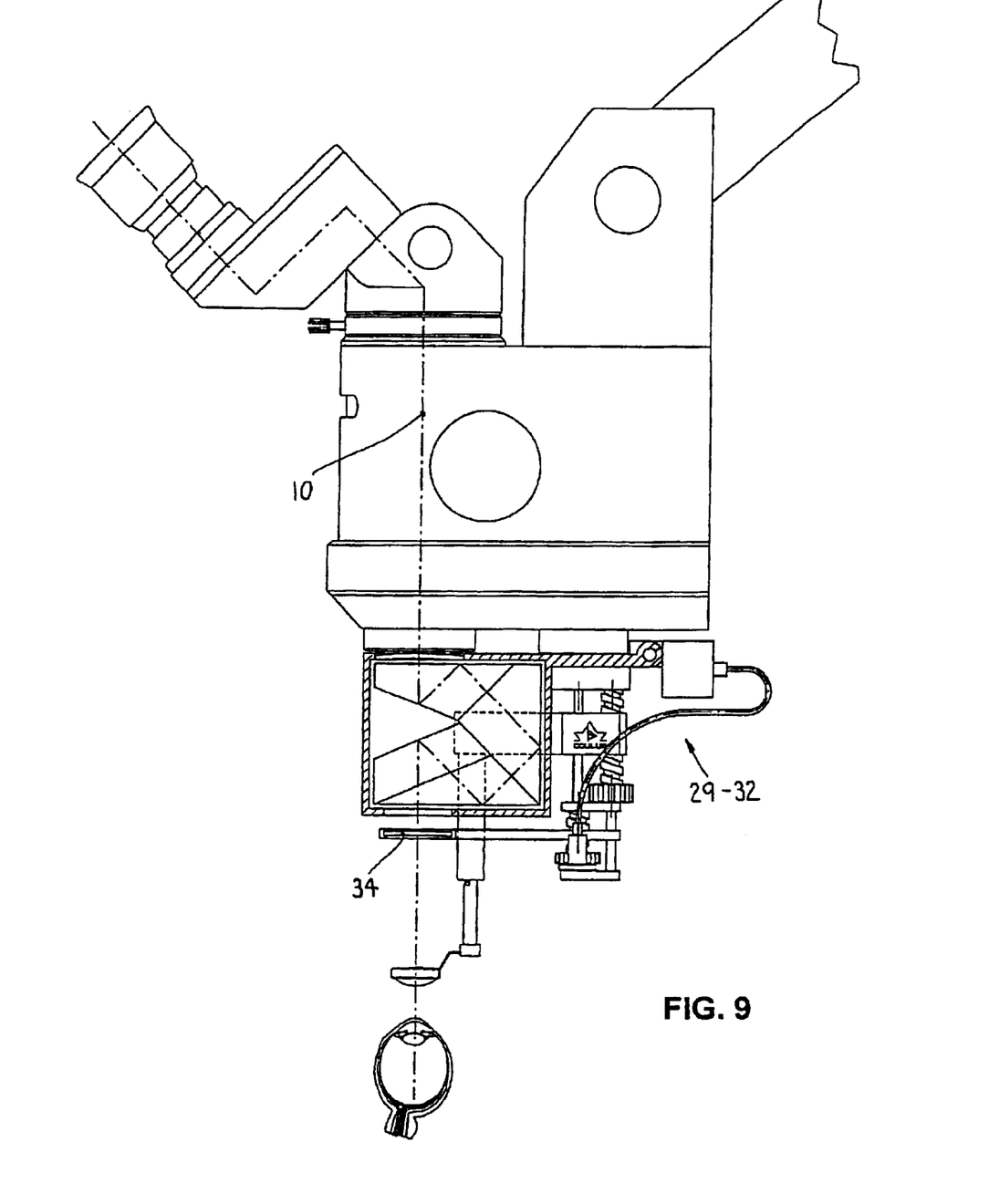
FIG. 9 illustrates a microscope according to FIG. 7 with an electrically drivable optical device to adjust the intermediate image.
Figure 10:
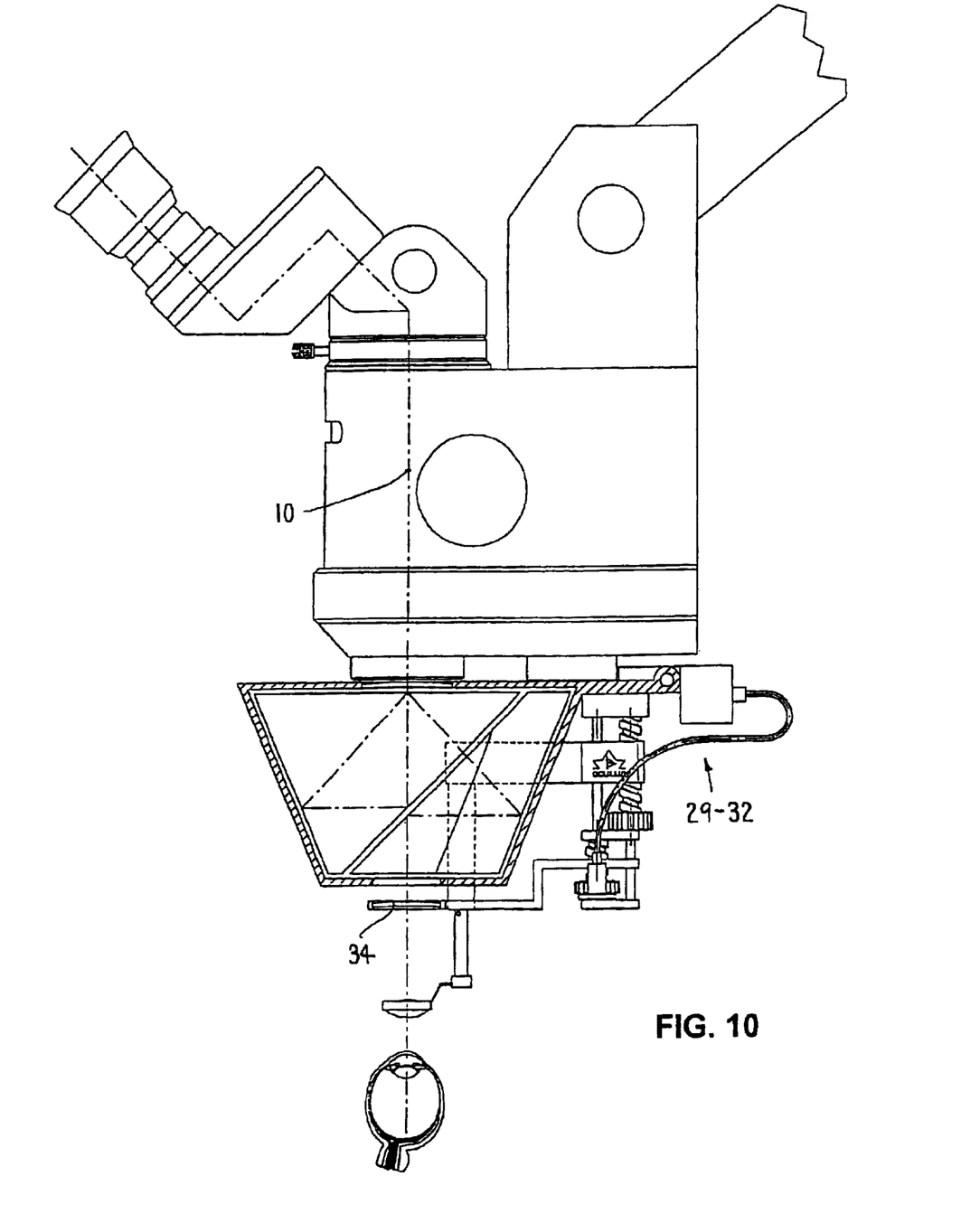
FIG. 10 illustrates a microscope according to FIG. 8 with an electrically drivable optical device to adjust the intermediate image.
Figure 11:
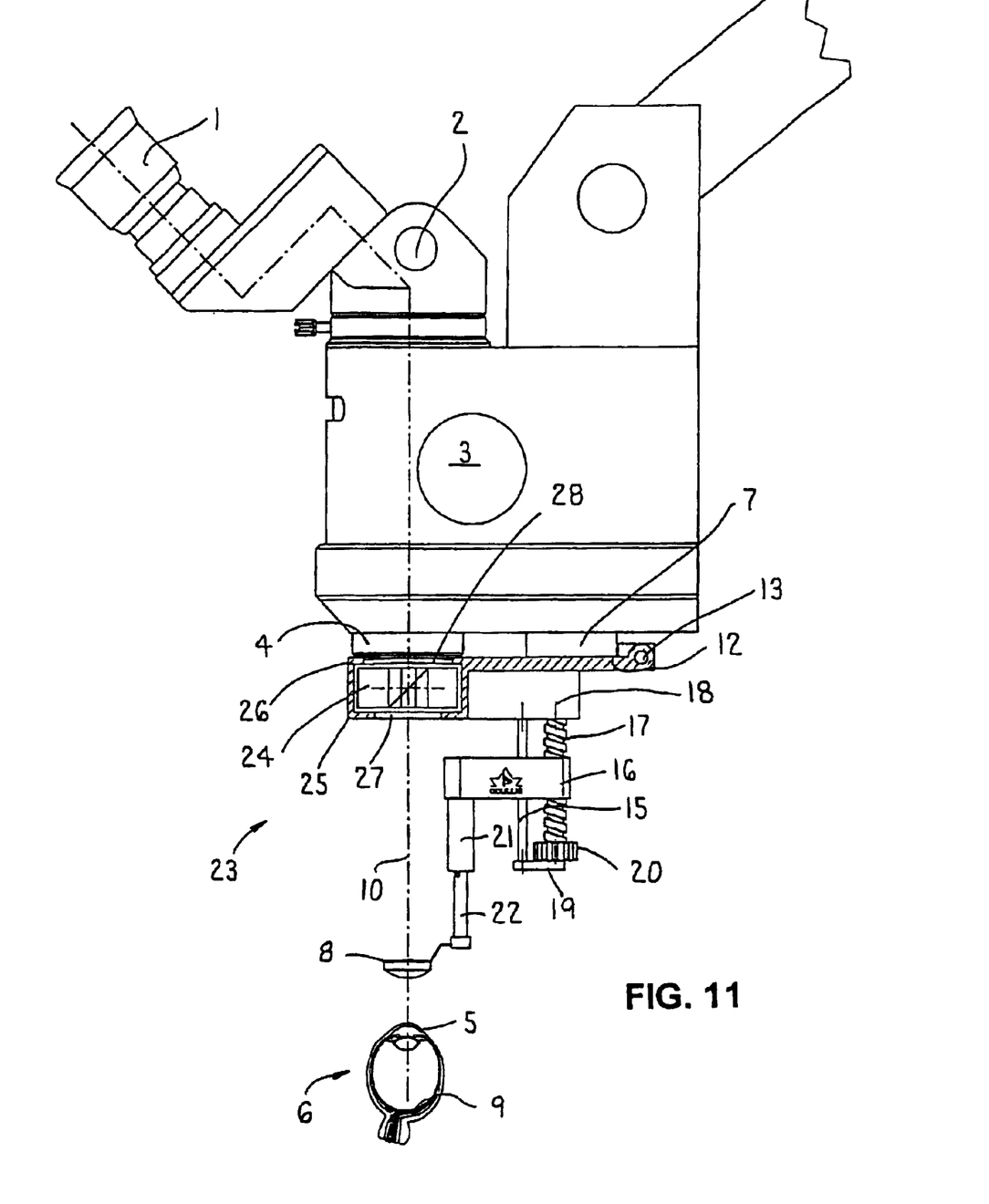
FIG. 11 illustrates a microscope according to FIGS. 1 to 5 with a Porro prism of the second type.
Figure 12:
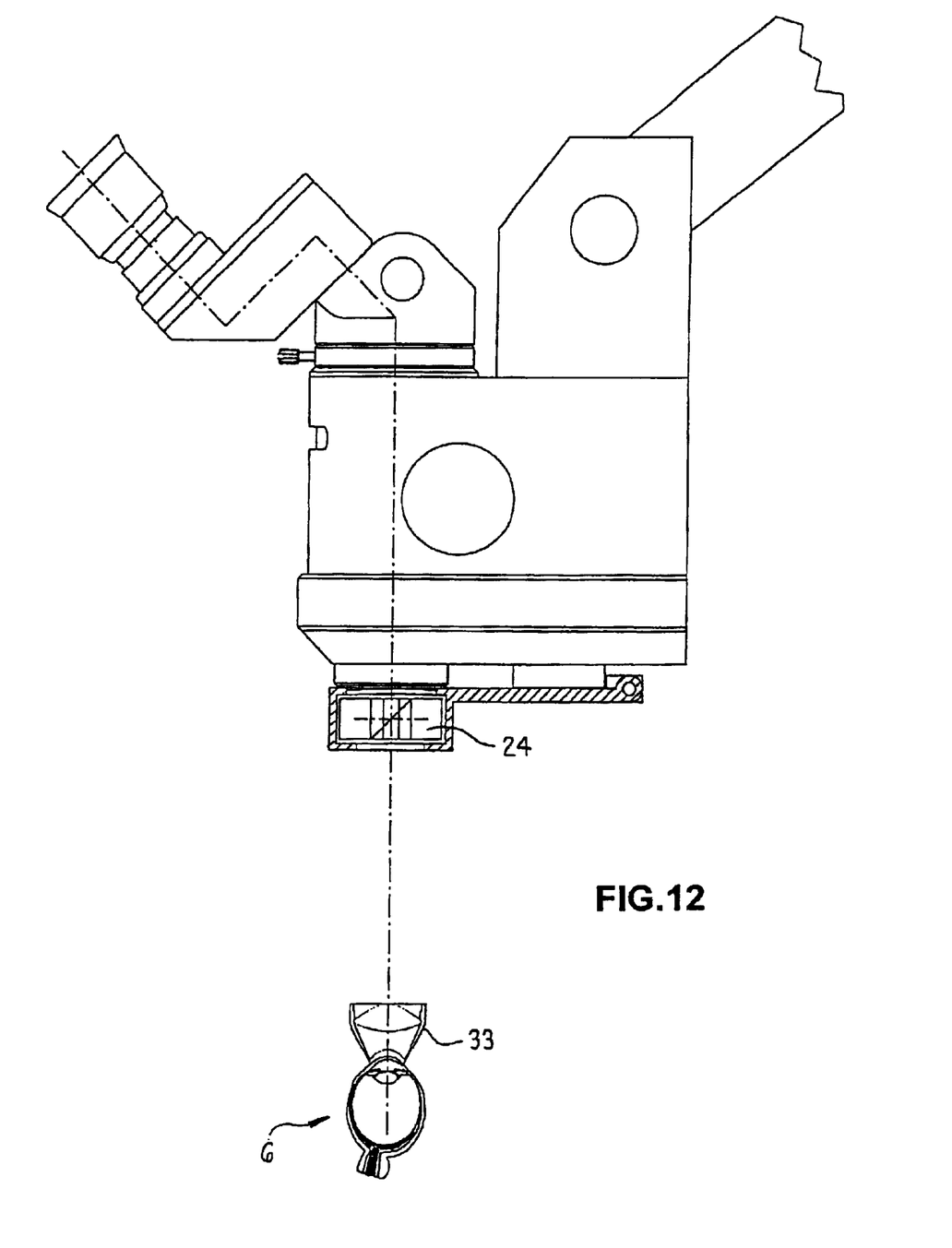
FIG. 12 illustrates a microscope according to FIG. 6, however, with a Porro prism of the second type.
Figure 13:
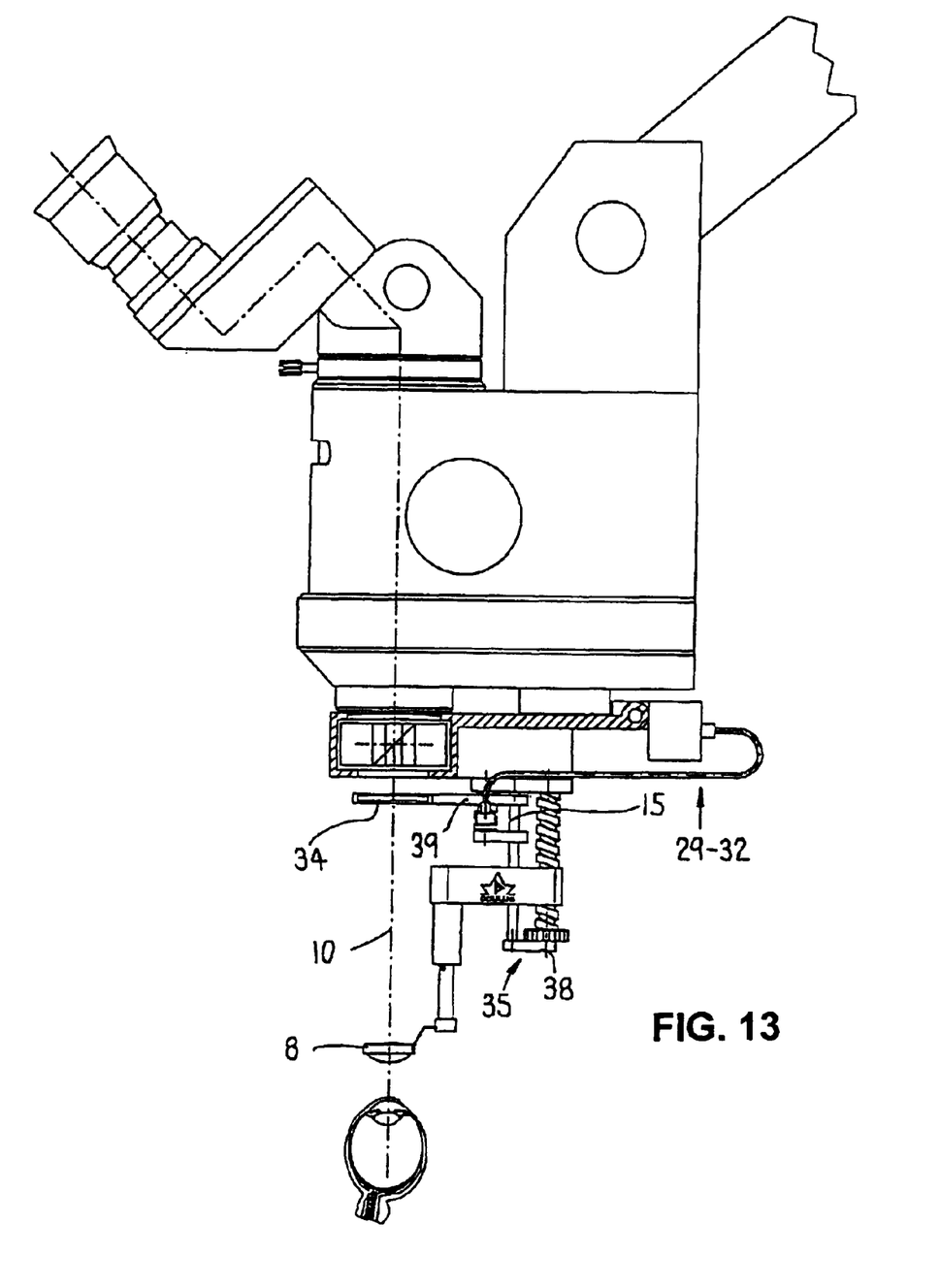
FIG. 13 illustrates a microscope according to FIG. 10, however, with a Porro prism of the second type.

A possibility to focus the optical device 8 without having to move it at all is offered by an additional optical device 34 movable along the beam path 10 to adapt the intermediate image according to FIGS. 7–10. In a similar manner as the optical device 8 for viewing the fundus of the eye 9, a second) spindle drive 35 is installed for the optical device 34, here a simple lens, whereby a further guide pin 36 and a threaded spindle 37 are each fastened at one end to a side of the first connecting plate 19 remote from the first spindle drive 11, and are held together at their respective other end by a (second) connecting plate 38. The optical device 34 is mounted on a (second) carriage 39 which, just like the first carriage 14, horses a segment which is moved by rotating the threaded spindle 37 in direction of the beam path 10 when a corresponding (second) control knob 40 secured to the threaded spindle 37 is operated (FIGS. 7, 8). The spindle drive 35 can, however, also be operated by means of the electric drive 29–32 corresponding to FIGS. 9, 10 in a similar manner as the spindle drive 11.

Figure 14:
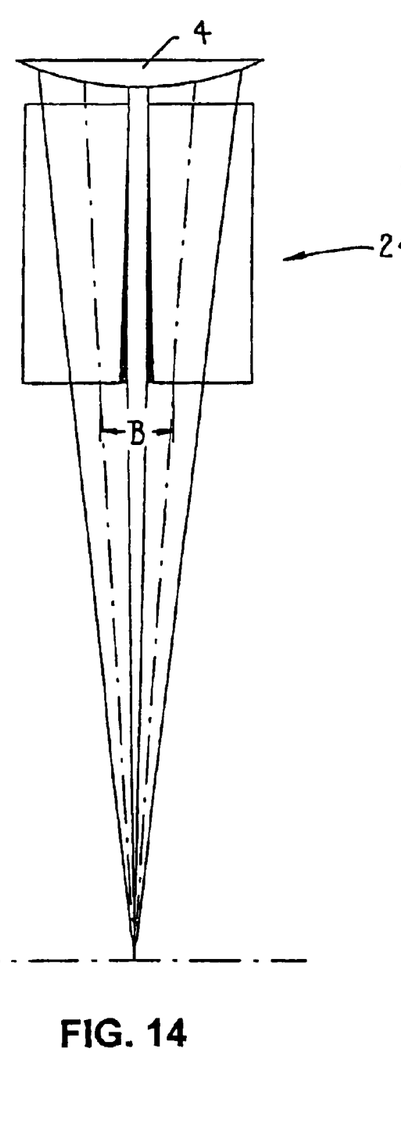
FIG. 14 illustrates the beam path in a microscope according to FIGS. 1 to 13.
Figure 15:
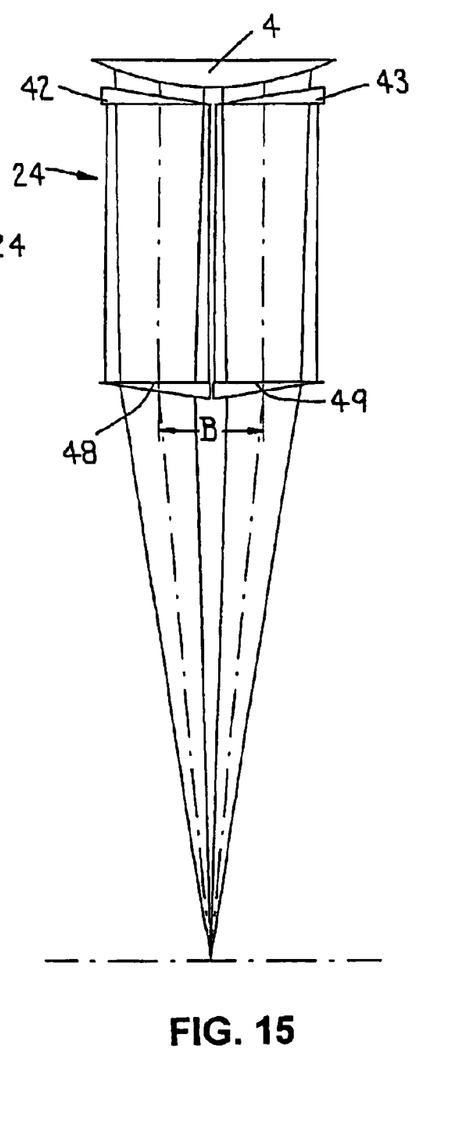
FIG. 15 illustrates the same beam path as in FIG. 14, however, with the utilization of four further prism systems.
Figure 16:
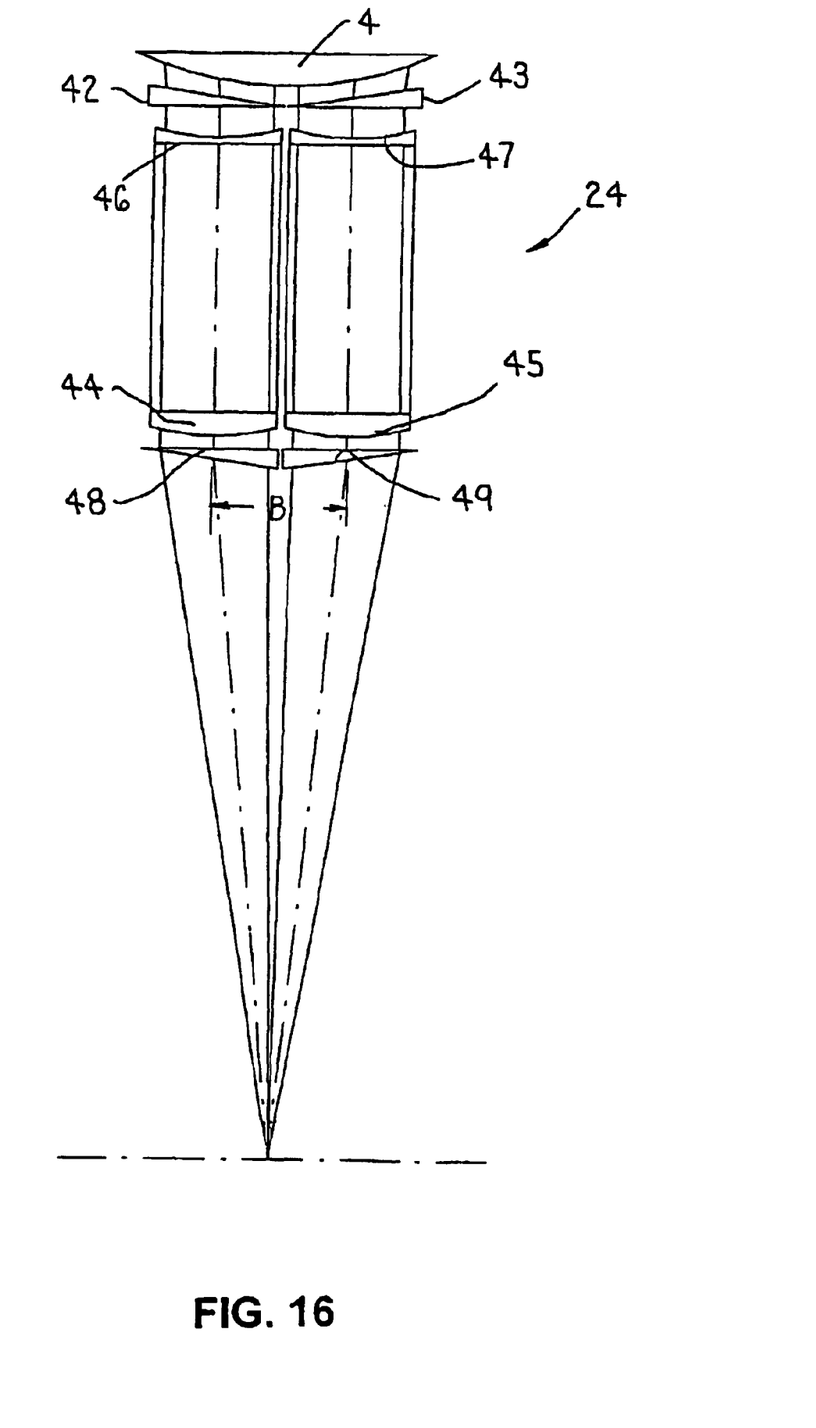
FIG. 16 illustrates the same beam path as FIG. 15, however, with the utilization of additional dispersing and focusing lenses, all in a schematic, simplified illustration.

The embodiment according to FIG. 14 illustrates the beam path below the microscope, whereby this beam path has been improved by the use of four prisms, as they are shown in FIGS. 15, 16. This results in particular in an enlargement of the stereoscopic base, whereby at the same time aberrations no longer exist. The advantage of this arrangement is that shadow effects cannot occur, and thus a better stereoscopic viewing is guaranteed. The prisms which are used are of equal strength, whereby the bottom base 5 of the prisms 40 and 41 are directed toward one another, whereas the prisms 42 and 43, which are closest to the lens 4, have their base directed outwardly. The stereoscopic width shown with the arrow B in FIGS. 15 and 16 is significantly improved by this arrangement over the width B in FIG. 14. The prisms have, for example at a lens width of 200 mm, advantageously 5 pdpt (prism dioptrin).

The prisms 42, 43, 48, 49 are in the exemplary embodiment according to FIG. 16 arranged below or above the prism system 24, whereby furthermore focusing lens 44, 45 or one dispersing lens 46 or 47 are each arranged between the prisms 42, 43, 48, 49. This further improves the image so that a parallel beam extent of the opening beams in the prism system is obtained. The operating distance from the entry surface is maintained and corresponds with the focal distance of the large lens 4.

What is claimed is:

1. A microscope for wide-angle viewing of an eye to be treated including a Porro prism system of the second type which has a small height, and is provided between a lens and the eye, said Porro prism for image reversion and image erection being configured to lie in a beam path of the microscope, and which is carried by a holder connected to the microscope so as to be moved or swung into the beam path of the microscope between the lens and the eye to be treated, wherein the Porro prism system is provided directly in front of the lens at a distance from the eye; a first optical device configured to be moved along the beam path by operation of a first spindle drive, the first spindle drive supporting a threaded spindle, wherein the first optical device is supported on a carriage which is guided longitudinally movably on a first guide pin mounted on the holder and extending parallel with respect to the first spindle drive, and wherein a first control knob for the first spindle drive is supported on the threaded spindle; and a second optical device configured to be moved along the beam path by a second spindle drive secured on a second guide pin in order to adjust an intermediate image, wherein the first guide pin is connected to the second guide pin through a connecting plate, and wherein a second control knob is provided for controlling the second spindle drive.

2. The microscope according to claim 1, wherein the holder is configured to be rotated about a swivel axle arranged on an underside of the microscope.

3. The microscope according to claim 2, wherein the swivel axle is provided approximately horizontally or vertically on the microscope.

4. The microscope according to claim 1, wherein the Porro prism system is arranged in a closed housing which has openings for the beam path.

5. The microscope according to claim 1, wherein between the Porro prism system and the lens there is provided a projection lens for adjusting the beam path, the projection lens being directly adjacent to the lens only when the prism system has been moved or swung into the beam path of the microscope.

6. The microscope according to claim 1, wherein the first and second control knobs are configured to be manually operated.

7. The microscope according to claim 1, wherein at least one of the control knobs is configured to be operated by an electric drive.

8. The microscope according to claim 7, wherein the electric drive includes an electric motor, an output of said electric motor being rotationally coupled to at least one of the first and second control knobs through a flexible shaft.

9. A microscope for the wide-angle viewing of an eye to be treated with a first optical device which is provided between a lens and the eye, and which creates a reversed image for facilitating a viewing of the fundus of the eye, and with a device for image reversion and image erection, said device for image inversion and image erection being configured to lie in a beam path of the microscope, wherein said device for image reversion and image erection comprises a prism system which has a small height, and which is carried by a holder connected to the microscope so as to be moved or swung into the beam path of the microscope between the lens and the eye to be treated, a second optical device movable lengthwise of the beam path and relative to the prism system, wherein the second optical device is provided in the beam path between the first optical device for viewing the fundus of the eye and the prism system.

10. The microscope according to claim 9, wherein the first and second optical devices are for at least one of wide-angle viewing and for an intermediate image, and are configured to be operated by manually or electromotively driven spindle drives.

11. A microscope for the wide-angle viewing of an eye to be treated with an optical device which is provided between a lens and the eye, and which creates a reversed image for facilitating a viewing of the fundus of the eye, and with a device for image reversion and image erection, said device for image reversion and image erection being configured to lie in a beam path of the microscope, wherein said device for image reversion and image erection comprises a prism system which has a small height, and which is carried by a holder connected to the microscope so as to be moved or swung into the beam path of the microscope between the lens and the eye to be treated, including first and second prisms lying essentially in a first plane and superposing the beam path, the first and second prisms being arranged in front of the prism system and closest to the lens, wherein prism bases of the first and second prisms are oppositely arranged so that the prism bases of each said prism do not face one another.

12. The microscope according to claim 11, wherein a dispersing lens is arranged between each said prism and the prism system, and wherein the dispersing lenses are adjacent to the lens of the microscope.

13. The microscope according to claim 12, including third and fourth prisms lying essentially in a second plane and superposing the beam path, said third and fourth prisms being arranged between the prism system and the eye to be viewed with the prism bases of the third and fourth prisms facing one another.

14. The microscope according to claim 13, including a pair of focusing lenses arranged between said prism system and said third and fourth prisms.

15. The microscope according to claim 11, including third and fourth prisms lying essentially in a second plane and superposing the beam path, said third and fourth prisms being arranged between the prism system and the eye to be viewed with the prism bases of the third and fourth prisms facing one another.

16. A microscope and attachment for wide-angle viewing of an eye, said microscope having a microscope lens at a lower end thereof defining a beam path and said attachment comprising:

a holder pivotally secured at a lower end of said microscope;

a prism system for image reversion and image erection, said prism system being secured to said holder and having a first opening at an end adjacent said microscope and a second opening at an opposing end;

a projection lens positioned in the first opening adjacent said microscope; and an optical device mounted to said holder and positioned between said prism system and an eye to be viewed, wherein said prism system, said projection lens and said optical device are pivotable from a position in the beam path of said microscope between the microscope lens and the eye to be viewed and a position out of alignment with the beam path of said microscope.

17. The microscope and attachment according to claim 16, including a guideway secured to said holder, wherein said optical device is adjustable in the direction of the beam path, said optical device being secured to a holding element that is received in said guideway.

* * * * *